United States Patent [19]

Carver

[11] Patent Number: 5,694,215
[45] Date of Patent: Dec. 2, 1997

[54] OPTICAL ARRAY AND PROCESSING ELECTRONICS AND METHOD THEREFOR FOR USE IN SPECTROSCOPY

[76] Inventor: David R. Carver, 20145 Hopi Pines Grove, Peyton, Colo. 80831

[21] Appl. No.: 610,663

[22] Filed: Mar. 4, 1996

[51] Int. Cl.[6] .................. G01N 1/10; G01J 3/00; G01J 3/42
[52] U.S. Cl. .................. 356/246; 356/300; 356/319
[58] Field of Search .................. 356/243–246, 356/410, 201–212, 195, 236, 331–334, 326, 300, 319, 417, 328, 188–190, 440; 250/226, 228; 204/180.1, 180.2, 180.9, 182.8; 422/68.1, 82.05

[56] References Cited

U.S. PATENT DOCUMENTS

| 4,029,419 | 6/1977 | Schumann, Jr. et al. | 356/173 |
|---|---|---|---|
| 5,021,646 | 6/1991 | Weinberger et al. | 250/227.11 |
| 5,037,199 | 8/1991 | Hlousek | 356/246 |
| 5,212,537 | 5/1993 | Birang et al. | 356/300 |
| 5,268,737 | 12/1993 | Fukuma et al. | 356/328 |
| 5,428,700 | 6/1995 | Hall | 372/32 |
| 5,434,664 | 7/1995 | Sapp | 356/244 |
| 5,439,578 | 8/1995 | Dovichi et al. | 204/299 |

*Primary Examiner*—Frank G. Font
*Assistant Examiner*—Michael P. Stafira
*Attorney, Agent, or Firm*—Timothy J. Martin; Michael R. Henson

[57] ABSTRACT

A sample cell assembly employs optics for focusing light though a sample cell, such as one used in electrophoresis. The optical array includes a first cylindrical lens having a central longitudinal axis in a common plane with the longitudinal axis of the sample cell. A second cylindrical lens has its central longitudinal axis oriented transversely to this common plane on another side of the sample cell from the first cylindrical lens. Preferably, a fiber optic beam splitter has a plurality of strands terminating in parallel second ends in the common plane so as to pass light at different longitudinally spaced locations through the sample cell cavity. Here, a plurality of second lenses receive the different light components to focus them respectively on different photodetectors each to create a sample data signal. Where a plurality of sample data signals are generated, processing electronics superimpose them to obtain an augmented signal of aggregate data. The invention further includes a method of measuring optical absorbance utilizing this technique and apparatus.

24 Claims, 4 Drawing Sheets

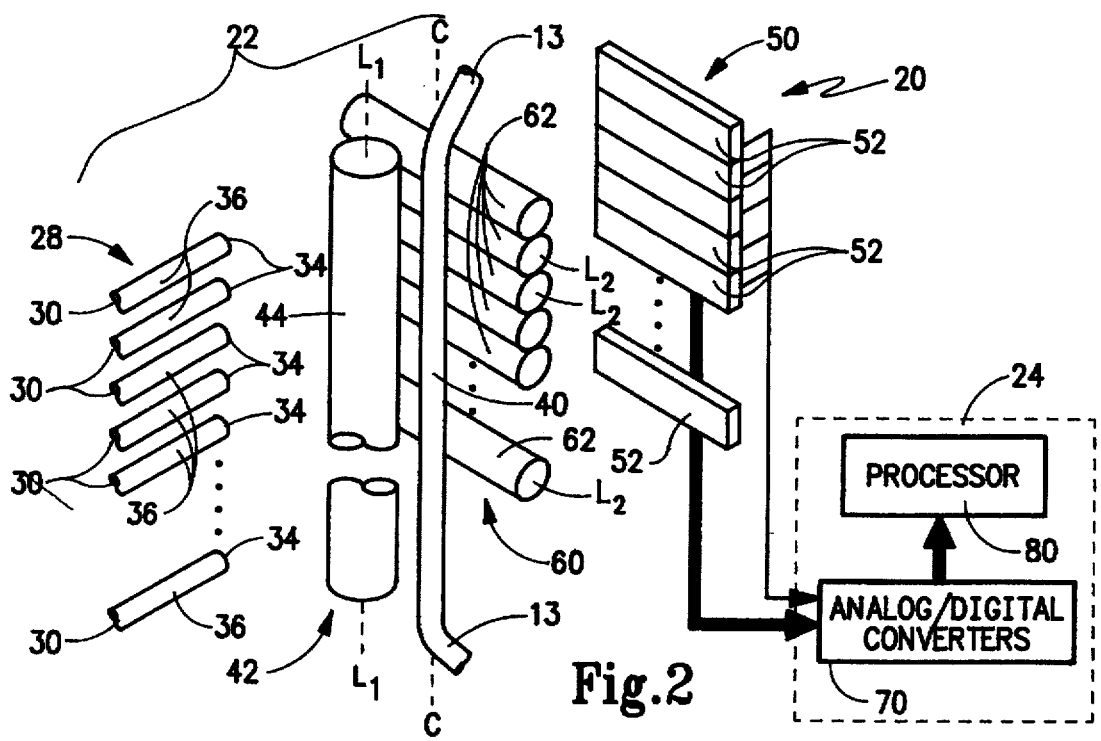
Fig.2
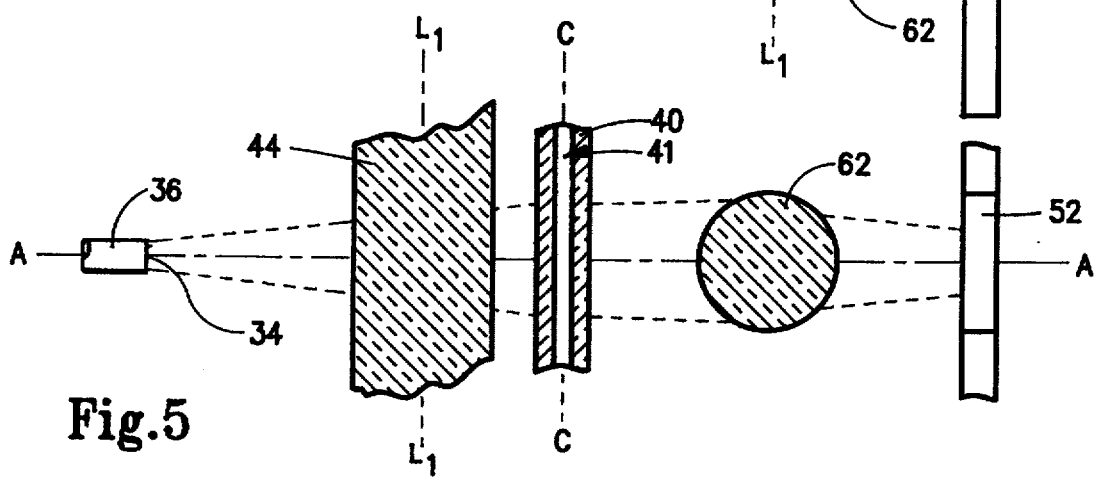
Fig.4
Fig.5

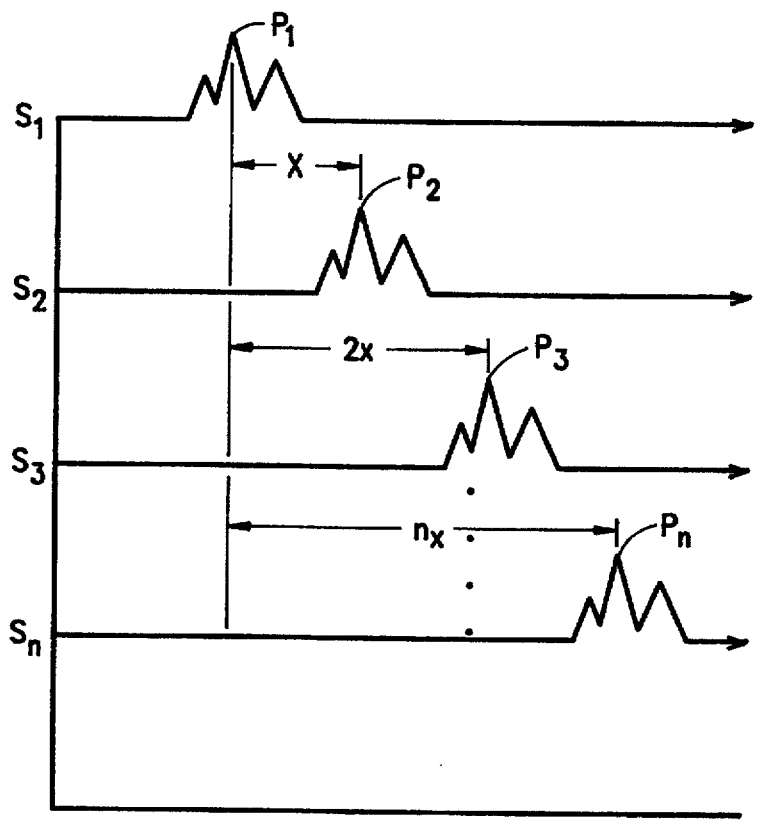
Fig. 7
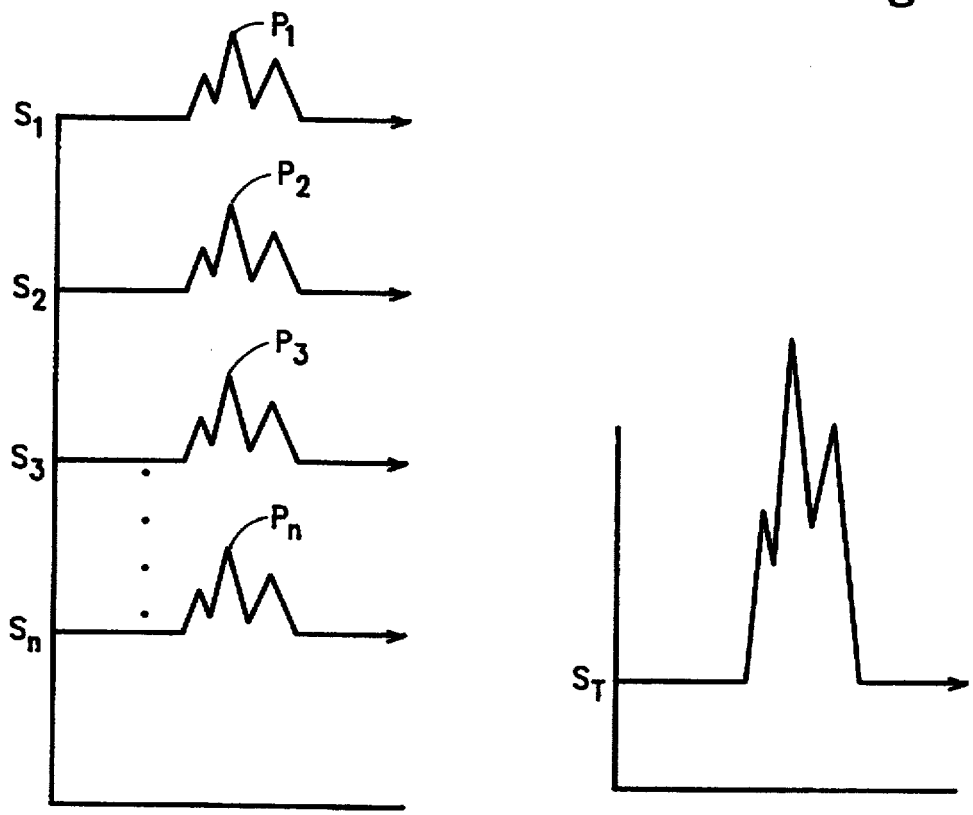
Fig. 8
Fig. 9

OPTICAL ARRAY AND PROCESSING ELECTRONICS AND METHOD THEREFOR FOR USE IN SPECTROSCOPY

FIELD OF THE INVENTION

The present invention is broadly directed to spectroscopy as an analytical tool to determine the optical properties of a material. More particularly, the present invention is directed to measuring the optical properties of a very small sample of material located in a sample cell. Specifically, this invention is directed to the field of capillary electrophoresis wherein the optical properties of a sample of small volume are measured in a dynamic flow state.

BACKGROUND OF THE INVENTION

A wide variety of analytical techniques are known to investigate the properties of a sample material. Among these, the response of a test sample to light of different wavelengths has received increasing attention as a means of identifying a compound contained within the test sample. These techniques, broadly referred to as chromatography, are of great interest to research analytical personal.

Typically, chromatography techniques are used in the separation of compounds which are mixed together in a complex system, such as an organic extraction. Here, it is desired to separate the system into its various constituents so that target compounds can be isolated and purified. In other applications, it is desired to detect the presence of a target compound in a test sample. One of the primary ways of identifying the nature of a compound during separation is through measuring the absorbance of the sample to light of known wavelengths. Especially useful is the measurement of the ultraviolet absorption of the test sample.

A widely used example of such separation and analysis is known as high pressure liquid chromatography (HPLC). A standard HPLC procedure comprises the passage of a test sample through a packed column of material, usually silica gel, under pressure. The various molecular compounds contained within the test sample may have slightly different flow velocities through the column so that, as the sample passes through the column, the various compounds begin to segregate from one another. Different discrete fractions of a sample may then be drawn at regular intervals to segregate the constituent compounds of the test sample. The identification of these compounds may then be achieved by chromatography. Naturally, separation of the compounds is important in chromatography so that the absorption pattern of one compound does not mask the absorption of another constituent compound.

Modern research techniques have exhibited a trend in the detection of smaller and smaller quantities of a compound in test sample and, moreover, the analysis of extremely small test samples for the presence of a target compound. These techniques employed, for example, in genetic research, bio-engineering, DNA testing, to name a few.

One technique of significant interest is known as capillary electrophoresis. Electrophoresis is a process for separating charged molecules based on their movement through a fluid under the influence of an applied electric field. In this technique, a background electrolyte is used as a carrier for the test sample with this background electrolyte being referred to as the "run buffer". The run buffer is used to provide for electrical conductivity unnecessary for the separation. Sometimes additive reagents may be employed to enhance separation of compounds within the test sample.

Significant among electrophoresis techniques is that known as high-performance capillary electrophoresis (HPCE) or simply capillary electrophoresis. Here, the carrier electrolyte is passed through a capillary tube of similar diameter under the influence of high driving voltage. The surrounding sidewall of the capillary tube supports the run buffer. When a test sample is introduced into the run buffer, compounds contained within the sample separate as they move through the capillary tube. HPCE has many desirable features. Analysis of the compounds in the sample can be made at near real time. The spectroscopic output is similar to that in regular chromatography, such as HPLC. Since HPCE is dynamic, the speed of separation is increased so that samples can be separated relatively quickly.

HPCE is not, however, without its difficulties. The demands on the designer of HPCE equipment are aggravated due to the extremely sensitive nature of the chemical separation and the extremely small volumes of sample that are being monitored in the capillary tube. Since the capillary tube typically has an interior diameter that may often be within a range of 50 to 100 micrometers with an outside diameter of about 350 micrometers, the ability to focus light on such a small volume is difficult. Directing light from a source, through the volume of interest and to a detector has generally been achieved using a lens or system of lenses to image the source into the volume contained in the capillary tube at a magnification that matches the image to the cross-sectional size of the volume contained therein. Such lensing systems have often been complex and require critical positioning of the capillary tube within the system.

A simplification of the lens system was proposed in U.S. Pat. No. 5,037,199 issued Aug. 6, 1991 to Hlousek. Here, the capillary tube is placed alongside a ball lens and is held in position by V-shaped channel structure. The ball lens is effective in focusing light through the sample in the capillary tube due to its relatively short focal length. As described in this patent, the ball lens converts the slowly converging light from the source into a rapidly converging cone of light that will image the source into or through the area of interest in the sample cell. This ball lens may also be used to focus the light exiting the sample onto a detector. The '199 Patent describes such a ball lens as being in the form of a sphere, a truncated sphere, a cylinder or a truncated cylinder.

Another attempt at a solution of detection involves the use of a "bubble" capillary tube to define the sample cell. Here, the sidewall of the capillary in the region of light transmission is increased by "bubbling" the capillary sidewall outwardly. This increases the cross-sectional dimension of the sample cell in this region so that the path length of light through the cell is increased. This allows the amount of light reaching the photodetector to be increased. Here, however, the voltage potential and the electrosmotic flow are disrupted so that the separation is not maximized.

Despite the state of evolution of the optical systems used in HPCE, there remains a need for improved detection techniques and improved optical arrays for capillary electrophoresis. There is also a need for HPCE equipment which can maintain good compound separation while increasing resolution of the detection of different compounds in the electrosmotic flow. There is also a need for such equipment to be able to perform extremely delicate and difficult separations. There is further a need for equipment which can enhance resolution, even under dynamic flow conditions.

SUMMARY OF THE INVENTION

It is an object of the present invention to provide a new and useful sample cell assembly incorporating an improved optical array for an elongated sample cell.

It is an object of the present invention to provide a new and useful method of measuring optical absorbance of a flowing sample material to obtain an augmented signal corresponding to the absorbance.

Another object of the present invention is to provide an optical array particularly adapted for use in spectroscopy of small volumes, especially in capillary chromatography.

A further object of the present invention is to provide a sample cell assembly and processing electronics therefore which can analyze test samples under dynamic flow conditions.

Yet another object of the present invention is to provide a sample cell array and processing electronics and a method embodying the same which can increase the spectroscopy resolution of the absorbance patterns of the compounds as they separate for chromatography.

Still a further object of the present invention is to provide a simplified lensing system for use in capillary electrophoresis apparatus.

It is still a further object of the present invention to provide a sample cell, optical array and processing electronics which may be incorporated into an analytical spectroscopic instrument in a cost efficient manner.

According to the present invention, then, an optical array is described for use with an elongated sample cell wherein the sample cell includes a sidewall surrounding a longitudinally extending cavity so that it has a longitudinal cell axis. In its broad form, this optical array includes a light source which emits a test beam of light for passage through the elongated sample cell. A fiber optic beam splitter is employed to direct light from the light source to the sample cell. The fiber optic beam splitter includes a plurality of fiber optic strands with these strands having first ends facing the light source to receive light therefrom and second ends opposite the first ends. The second ends terminate in parallel second end portions that are organized in a common plane also containing the longitudinal cell axis with the second ends of the fiber optic strands facing the sample cell. A first lens system is interposed between the second ends of the fiber optic strands and is operative to focus light exiting from the second ends into the longitudinally extending cavity at different longitudinally spaced locations therealong. A plurality of photodetectors is arranged in a column, with each photodetector being operative to receive light from a respective one of a fiber optic strands thereby to generate a signal corresponding to the received light. A second lens system is then interposed between the sample cell and the photodetectors with this second lens system being operative to focus light passing through the cavity onto the photodetectors.

It is preferred that the first lens system include a first cylindrical lens having a first central longitudinal axis oriented in a first common plane with the longitudinal cell axis and located on one side of the sample cell. The second lens system preferably includes an array of second cylindrical lenses on another side of the sample cell. Each of the second cylindrical lenses has a second longitudinal axis with these second central longitudinal axes being oriented in a second common plane with one another. This second common plane is oriented perpendicularly to the first common plane. The second cylindrical lenses are preferably in one-to-one numerical correspondence with the photodetectors, and processing circuitry is provided to process signals from the photodetectors. Preferably, this signal processing circuitry includes an analog-to-digital converter associated with each photodetector.

The present invention also contemplates a sample cell assembly adapted for use in the spectroscopy of sample volumes in capillary chromatography. Accordingly, the invention includes an elongated sample cell that has a sidewall surrounding a longitudinally extending cavity that is operative to receive a sample volume. Preferably, the sample cell is a capillary tube and a plurality of light emitters are provided each operative to produce a beam of light along a respective optical axis that intersects the longitudinal axis of the sample cell. The light emitters may comprise the second ends of a fiber optic beam splitter, as described above, and similar focusing optics may be employed.

Preferably, the processing electronics employed to monitor the output of the photodetectors, as noted above, employs an analog-to-digital converter for each separate photodetector in the detection array. Accordingly, as a segment of the solution passes through the region monitored by each emitter and detector pair, a corresponding spectral pattern for absorbance will be produced. The processing electronics then superimpose the plurality of spectral patterns to result an enhanced signal that sums all of the outputs of the detectors corresponding to its measurement of the respective sample. The processing electronics may superimpose the signals either by monitoring the velocity of fluid flow through the capillary tube and shifting the respective signals from each detector according to this velocity or by determining a reference peak in the spectral pattern, such as the maximum spectral peak and then superimposing the signals utilizing this reference peak for each of the independent measurements.

According to the broad method of the present invention, then, optical absorbance of light through a volume of a sample material flowing in a flow direction through a sample cell is provided. This method broadly comprises of the steps of passing a plurality of test components of light through the sample cell. Each of the test components is passed along an optical axis that is in a direction transversely to the flow direction, and each test component is directed through differently spaced locations along the sample cell. The method then includes the step of providing a detector for each of the test components of light with each detector being operative to generate a detector output signal corresponding to the intensity of a respective test component. Finally, the method includes shifting the phase of the detector output signals and thereby superimposing the detector output signals to create an augmented detector signal. The method may include the step of converting analog signals from the detectors into digital signals prior to shifting the phase thereof.

The shifting of phase according to the preferred method may be accomplished by alternative steps. On one hand, the phase shift may be accomplished by measuring the velocity of the sample material through the sample cell in the flow direction and thereafter shifting each detector signal temporally in an amount proportional to its space location in the velocity of the sample material. On the other hand, the phase shift can be accomplished by identifying a target feature of each detector signal and shifting the detector signal to superimpose the target features with one another. In any event, it is preferred that the plurality of test components of light be generated by a single light source that is thereafter split into the test components, for example, by the fiber optic beam splitter described above. Further, it is desired that the test components have optical axis that are parallel to one another. Finally, the method may include the step of displaying the augmented detector signal.

These and other objects of the present invention will become more readily appreciated and understood from a consideration of the following detailed description of the exemplary embodiment when taken together with the accompanying drawings, in which:

BRIEF DESCRIPTION OF THE DRAWINGS

FIG. 2 is a perspective view of a portion of the optical array used in the detector of the present invention along with the processing electronics therefore being shown in diagrammatic form;

FIG. 4 is a diagrammatic view in cross-section of the exemplary embodiment of the present invention looking along central longitudinal axis of the capillary tube;

FIG. 5 is a diagrammatic view in cross-section, similar to FIG. 4, but looking along an axis that is perpendicular to the central longitudinal axis of the capillary tube and perpendicular to the optic axis of a test beam of light from an emitter;

FIG. 7 is a graph of a signal set from an array of detectors according to the exemplary embodiment of the present invention, in diagrammatic form;

FIG. 8 is a graph of the signal output shown in FIG. 7, but being conditioned for super positioning;

FIG. 9 shows the super imposed signals of FIGS. 7 and 8; and

DETAILED DESCRIPTION OF THE EXEMPLARY EMBODIMENTS

Figure 1:
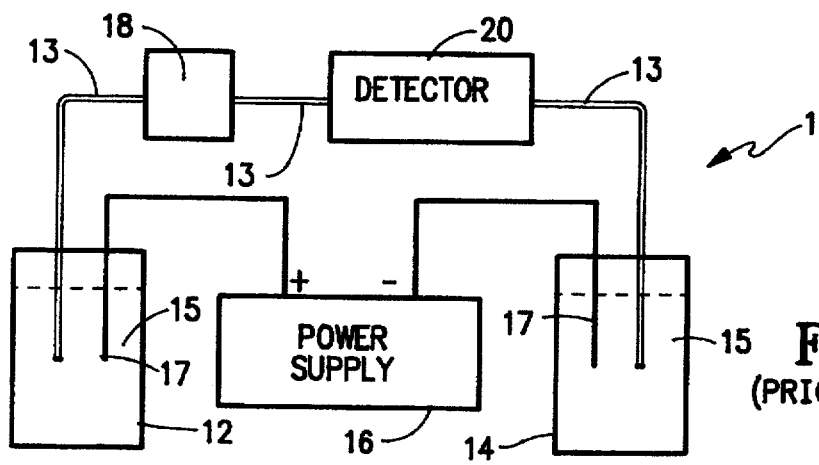
FIG. 1 is a diagrammatic view of a system employed for capillary electrophoresis according to the prior art.

The present invention is directed to an optical array and processing electronics particularly useful for spectroscopy. Accordingly, the present invention is directed to a sample cell assembly for spectroscopy. While the present invention is particularly adapted and is described for use with capillary electrophoresis, it should be understood that the present invention is not limited to strictly to electrophoresis only. Indeed, other applications which may employ the present invention include capillary gas chromatography, capillary HPLC and other techniques where the need to monitor the absorbance of light through small tubes or small sample cells is necessary. Broadly, the present invention includes new and useful focusing optics for focusing multiple beams of light into and through either a sample cell or a capillary tube interior at different longitudinally spaced locations therealong. This technique allows for sequential or concurrent testing of a sample for optical absorbance at one or more wavelengths. Moreover, the present invention broadly includes processing electronics such that, where a compound in a separation is under dynamic flow through the sample cell, as would be the case for capillary electrophoresis, multiple absorbance spectra may be obtained for a given segment and super imposed to yield a combined signal of greater resolution. The present invention is specifically described with respect to capillary electrophoresis. However, it is to be understood that the principles taught may be employed with other systems to be determined by the ordinarily the skilled person in the field of invention. Turning, then, to FIG. 1, it may be seen that a diagram of a typical prior art capillary electrophoresis system is depicted. Here, capillary electrophoresis system 10 includes a first buffer reservoir 12 and a second buffer reservoir 14 which are maintained at a substantial potential difference by power supply 16. Power supply 16 preferably maintains this potential difference at about 30,000 volts by way of electrodes 17. A capillary tube 13 extends between reservoir 12 and reservoir 14 so that fluid flow may pass therethrough for the buffer solution 15 contained in the two reservoirs. As is known, capillary tube 13 has an internal diameter on the order of about 50–100 micrometers and an outside diameter of approximately 350 micrometers. A detector 20, described more thoroughly below, is interposed to monitor test samples which are separated by the capillary electrophoresis as they are carried by the buffer solution. These samples may be introduced at an injector station 18 of any type known in the art.

Figure 3:
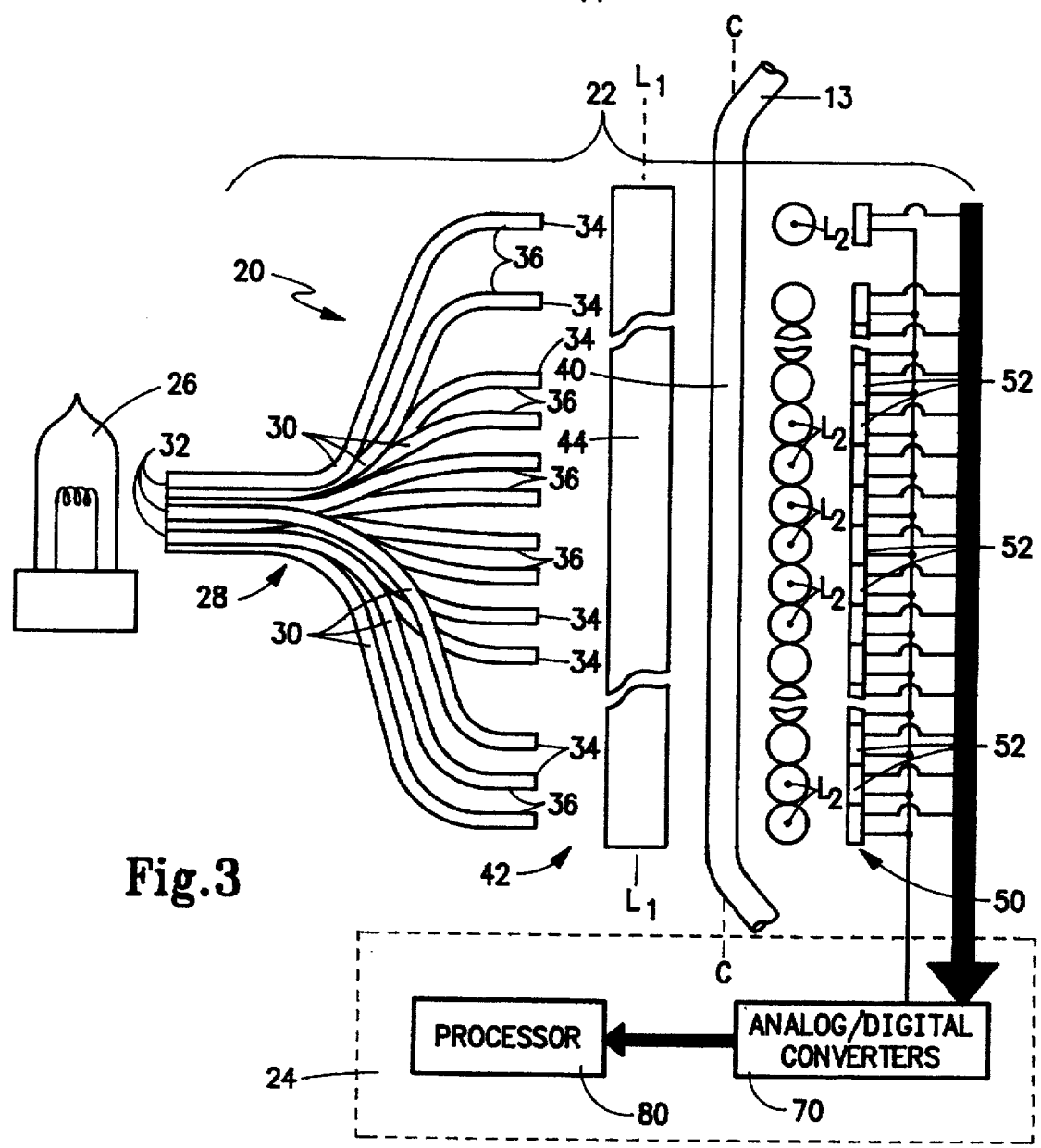
FIG. 3 is a diagrammatic view showing the sample cell and optical array of the exemplary embodiment of the present invention connected to processing electronics therefore.

Detector 20, according to the preferred embodiment of the present invention is best shown in FIGS. 2 and 3. Here, detector 20 includes an optical array 22 and processing electronics 24 which monitors the output of optical array 22. Optical array 22, in turn, includes a light source 26, of any suitable selected wavelength or any combination thereof for producing light at a desired wavelength at which the chromatograph is to be made. Typically, ultraviolet light may be employed for absorption measurements.

Light emitted by light source 26 passes into a fiber optic beam splitter 28 comprising a plurality of separate fiber optic strands 30. Each fiber optic strand 30 has a first end 32 which faces the light source to receive light emitted therefrom and second ends 34 opposite first ends 32. Each fiber optic strand 30 has a second end portion 36 which is proximate to second end 34 with second end portions 36 being organized in a common plane. A portion of the capillary tube 13 forms a sample cell 40 which is oriented along a longitudinal cell axis "C". The common plane defined by second end portions 36 contain this longitudinal cell axis with the second ends 34 facing the sample cell 40.

A first lens system 42 is interposed between second ends 34 of fiber optic strands 30 with this first lens system being operative to focus light exiting the second ends 34 into the cavity located within sample cell 40 at different longitudinally spaced locations therealong. As is shown in FIGS. 2 and 3, first lens system 42 is preferably in the form of a first cylindrical lens 44 having a first central longitudinal axis "$L_1$" that is oriented in the first common plane along with the longitudinal cell axis and the second end portions 36. Preferably, first central longitudinal axis "$L_1$" is parallel to the longitudinal cell axis "C". The spacing of second ends 34 of fiber optic strands 30, sample cell 40 and cylindrical lens 44 and the focal length of cylindrical lens 44 so that the light which is emitted from each of second ends 34 is focused on the interior of sample cell 40. Naturally, this positioning must take into account the index of refraction of the material forming both the sample cell and the cylindrical lens, as is well-known to the ordinarily skilled optical designer. After passing through sample cell 40, each test component of light corresponding to each fiber optic strand 30 is focused onto a photodetector 52 organized in photodetector array 50.

Accordingly, it is preferred that photodetectors 52 be in one-to-one correspondence with fiber optic strands 30. Further, a second lens system 60 is interposed between sample cell 40 and array 50 of photodetectors 52 with second lens system 60 being operative to focus light passing through sample cell 40 onto the photodetector array 50. As again seen in FIGS. 2 and 3, it is preferred that second lens system 60 be formed of a plurality of cylindrical lenses 62 located on a side of sample cell 40 opposite cylindrical lens 44. Here, cylindrical lenses 62 have second central longitudinal axes "$L_2$" which are oriented in a second common plane with respect to one another. This second common plane, however, is oriented perpendicularly to the first common plane but parallel to both central longitudinal axis "$L_1$" of first cylindrical lenses 44, therefore, parallel to central axis "C" of sample cell 40. With this orientation, the axes "$L_2$" are transverse to the first common plane. While it is preferred that they intersect the first common plane at right angles, a large oblique angle would also be acceptable.

Here, again, the spacing of photodetector array 50 and cylindrical lenses 62 are such that light exiting the sample cell 40 corresponding to each fiber optic strand 30 is focused on a respective photodetector 52. Accordingly, it is preferred that cylindrical lenses 62 be in one-to-one correspondence both with fiber optic strands 30 and photodetectors 52. Thus, each respective fiber optic strand 30, each second cylindrical lens 62 and each photodetector 52 form an independent fiber optic set to define an independent optical test path so that multiple test signals may be produced as a test sample dynamically flows through capillary tube 13 and, specifically, through the region defined as sample cell 40. It should be understood that first cylindrical lens 44 forms a common focusing lens for the emitters of each of the fiber optic sets, with these emitters comprising the second end portions 36 of fiber optic strands 30. However, it should also be understood to the ordinarily skilled person in this field that an independent focusing lens could be used to focus light from each emitters. Thus, each fiber optic set, as defined above, includes a longitudinal segment of first cylindrical lens 44.

In any event, the light detected by each of photodetectors 52 may be suitably processed by processing electronics 24. With reference to FIGS. 2 and 3, it may be seen that processing electronics 24 includes a set of analog-to-digital convertors 70 as well as a processor 80 which receives digital signals from analog-to-digital convertors 70 to process those signals to create a spectral pattern corresponding to the absorption pattern detected by each photodetector 52.

With reference now to FIGS. 4 and 5, the relative spacing of a selected optical array is depicted. Here, it may be seen that light emitted from a selected emitter in the form of second end 36 of fiber optic strand is divergent onto cylindrical first lens 44. Cylindrical first lens 44 focuses the lateral portions of this light beam into cavity 41 of sample cell 40, as is best shown in FIG. 4. Longitudinal portions of this beam, however, do not converge with one another. As the light beam exits cavity 41, it is again divergent and impinges on a respective second cylindrical lens 62. Here, however, the lateral portions are not substantially further focused, as is shown in FIG. 4. Rather, as is shown in FIG. 5, the longitudinal portions of the light beam are not convergent onto a respective photodetector 52.

Figure 6:
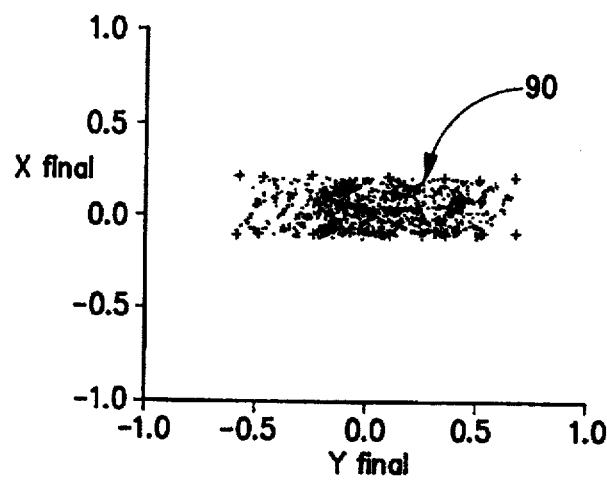
FIG. 6 is a graph showing the x/y distribution pattern of a test beam of light that is focused on a photodiode detector according to the exemplary embodiment of the present invention.

The resulting focused light pattern 90 according to these focusing optics is shown on the graph depicted in FIG. 6. With the array shown in FIGS. 4 and 5, the resulting pattern 90 on each photodetector 52 has a width of approximately 1 millimeters and a height of approximately 0.5 millimeters. This gives a very uniform spectral pattern for measurement by each photodetector 50.

From the above description, it may be appreciated that multiple test optical paths are provided through sample cell 40, as determined by the number of emitters defined by fiber optic strands 30. It is desired that either 20 or 38 optical sets be employed since there are commercially available photodiode arrays with either 20 or 38 elements. Such arrays are readily available from United Detector Technology of Los Angeles, Calif. In this array, each photodiode element is approximately 1 millimeters by 4 millimeters in area. Accordingly, spectral pattern 90 is readily compatible with each of these photodiode elements. It should be fully understood, however, that the present invention is not limited to a specific number of optical sets so that the principles contained herein may be employed with different numbers of optical sets as determined by the designer or the detector 20.

With reference now to FIGS. 7-9, it may be seen that representative signals $S_1$, $S_2$, $S_3$, ... $S_n$, which are derived from each optical set as a component segment passes through the sample cell 40 that will be produced by the processing electronics 24. These signals are shifted a distance "nx" where "n" is an integer, depending upon the velocity of flow of the test component through the sample cell. This is illustrated in FIG. 7 which shows the signals for each successive detected signal from the array of analog-to-digital converters 70. In FIG. 8, it may be seen that signals $S_1$–$S_{10}$ are registered with one another by processor 80. This can be accomplished in one of two ways. One technique is accomplished by monitoring the velocity of the fluid flow and adjusting each respective signal, its corresponding "nx" distance. Alternatively, monitoring electronics may note a reference point in the signal, such as peak $P_1$, $P_2$, $P_3$, etc. and register these peaks or other reference points so that the signals are in phase with one another. Processor 80 may then superimpose these signals, as is shown in FIG. 9, to create an enhanced or augmented detector signal with greater resolution as signal $S_r$.

Figure 10:
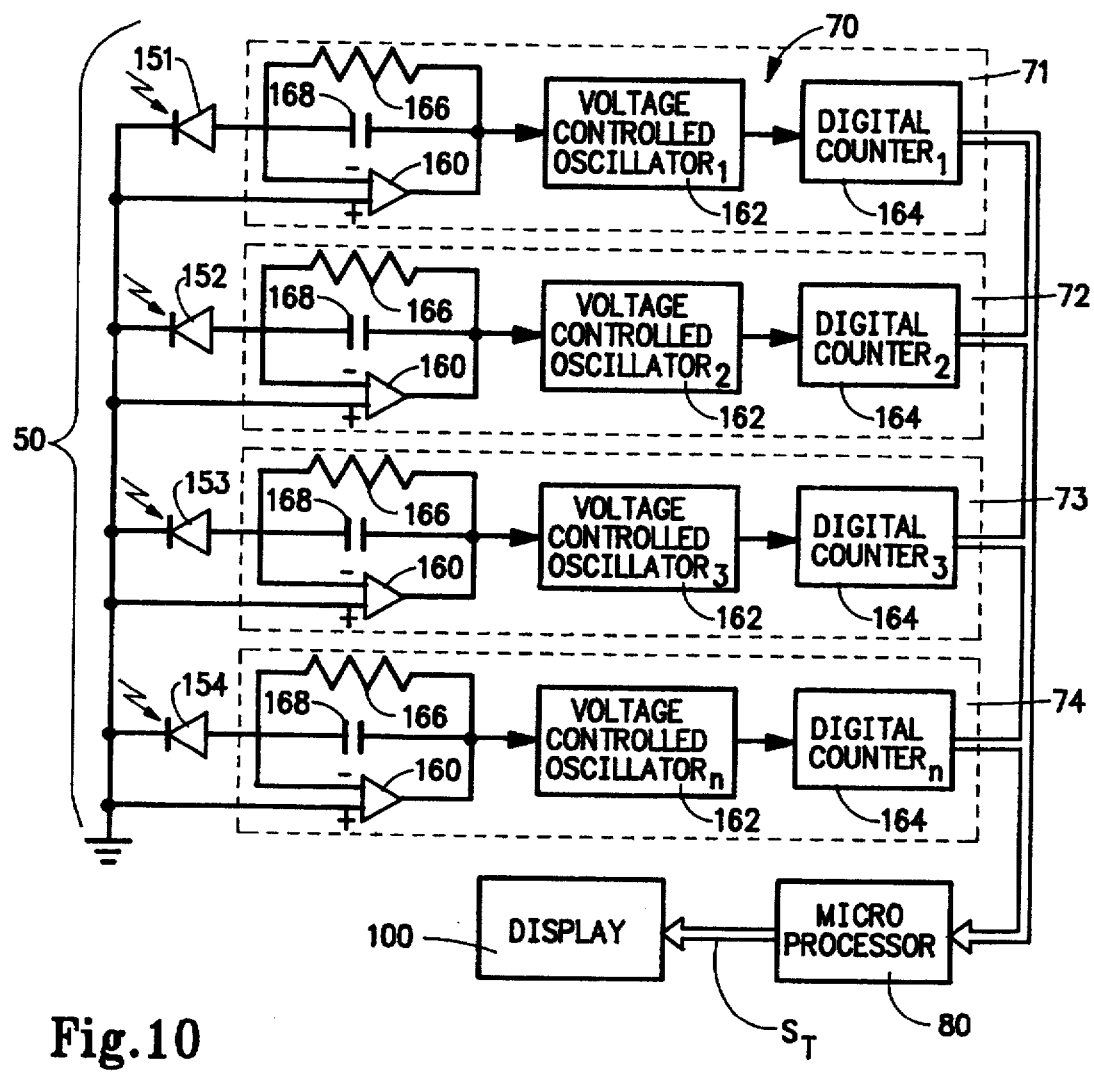
FIG. 10 is a diagrammatic view of the processing electronics which may be employed in the exemplary embodiment of the present invention.

A flow chart diagram of the processing electronics is shown in FIG. 10. Here, analog-to-digital converters 71, 72, 73 and 74 comprise analog-to-digital converter array 70 which respectively receive inputs from photodiode array 50 which includes photodiodes 151, 152, 153 and 154. These signals are then passed to a microprocessor 80 incorporating suitable software to process the signal to create the combined signal $S_r$ (FIG. 9) and output this data on any suitable output device 100. The electronics for such a device employs conventional circuitry, as is known to the ordinarily skilled person in this field.

With reference again to FIG. 10, it may be seen that each of the analog-to-digital converters 71-74 includes a transimpedience operational amplifier 160, a voltage controlled oscillator 162 and a digital counter 164. A resistor 166 and a capacitor 168 are connected in parallel to one another across the input and output of each operational amplifier 160, with each resistor 166 and each capacitor 168 accordingly forming a low pass filter for the operational amplifier 160. The time constant of the low pass filter is then "R" times "C". It is preferred to operate the system at relatively low frequency, such as approximately 100 Hertz. Accordingly, the rise time of the photodiode and the linearity of the response of the operational amplifier do not need to be augmented by reverse biasing the operational amplifier. To do so, would increase the dark current and noise level of the circuitry. The operational amplifier may be any component readily available, such as an OPA 111 circuit chip. Likewise, depending upon cost concerns, it is possible to acquire the analog-to-converter in a single chip, such as the AD7710, or any suitable equivalent. Naturally, of course, separate circuit components could be used for the voltage controlled oscillator and for the digital counter, if desired, although single chip may be preferred for simplicity.

From the foregoing, it may be appreciated that the present invention also contemplates a method of measuring optical absorbance of light through a volume of sample material flowing in a flow direction through a sample cell. The broad method includes the first step of passing a plurality of test components of light through the sample cell. Each of these test components has an optical axis in a direction transversely through the flow direction of the sample material, and each pass through at different spaced location therealong. Preferably, these test components may come from a single beam of light that is split, for example, by the beam splitter above, into the test components. Moreover, it is preferred that the optical axis of the test components be parallel to one another. Next, the method includes the step of providing a detector for each of the test components of light with each detector being operative to generate a detector output signal corresponding to the intensity of a respective test component. Finally, the broad method includes the step of shifting the phase of the detector output signals and superimposing the detector output signals to create an augmented detector signal that is the sum of all of the signals from the test components.

The phase shifting is accomplished in one of two preferred ways. On one hand, one can monitor the velocity of the flow of the sample material through the sample cell in the flow direction so that the detector signal is shifted temporally in an amount proportional to its space location along the sample cell and the velocity of the sample material. Alternatively, the step of shifting phase may be accomplished by identifying a target feature of each detector signal, such as a leading edge of a spectral absorbance pattern or a maximum peak in the spectral absorbance pattern and thereafter shifting the detector signal to superimpose the target features with one another. Preferably, the detector signals from the photodiodes are analog signals and the method includes the step of converting each detector signal separately into a digital signal prior to shifting the phase thereof. Moreover, if desired, one of the test signals can be a reference signal from providing a reference intensity of a test component of light for purposes of monitoring the output of test signals passing through the sample cell.

Accordingly, the present invention has been described with some degree of particularity directed to the exemplary embodiment of the present invention. It should be appreciated, though, that the present invention is defined by the following claims construed in light of the prior art so that modifications or changes may be made to the exemplary embodiment of the present invention without departing from the inventive concepts contained herein.

I claim:

1. An optical array for use with an elongated sample cell including a sidewall surrounding a longitudinally extending cavity and having a longitudinal cell axis, comprising:
   (a) a light source;
   (b) a fiber optic beam splitter including a plurality of fiber optic strands, said strands having first ends facing said light source to receive light therefrom and second ends opposite said first ends, said second ends terminating in parallel second end portions that are organized in a common plane containing the longitudinal cell axis such that said second ends face the sample cell;
   (c) a first lens system interposed between the sample cell and the second ends of said fiber optic strands and operative to focus light exiting said second ends into the cavity at different longitudinally spaced locations therealong;
   (d) a plurality of photodetectors arranged in a column, each said photodetector operative to receive light from a respective one of said fiber optic strands and to generate a signal corresponding thereto; and
   (e) a second lens system interposed between the sample cell and said photodetectors and operative to focus light passing through said cavity onto said photodetectors.

2. An optical array according to claim 1 wherein said first lens system includes a first cylindrical lens having a first central longitudinal axis oriented in a first common plane with the longitudinal cell axis on one side of said sample cell.

3. An optical array according to claim 2 wherein said second lens system includes an array of second cylindrical lenses on another side of said sample cell, each of said second cylindrical lenses having second central longitudinal axes oriented in a second common plane with one another, the second common plane being oriented perpendicularly to the first common plane.

4. An optical array according to claim 3 wherein said second cylindrical lenses are in one-to-one numerical correspondence with said photodetectors.

5. An optical array according to claim 1 including signal processing circuitry operative to process signals from said photodetectors, said signal processing circuitry including an analog-to-digital converter associated with each photodetector.

6. A sample cell assembly adapted for use in spectroscopy of sample volumes in capillary chromatography, comprising:
   (a) an elongated sample cell including a sidewall surrounding a longitudinally extending cavity that is operative to receive a sample volume, said sample cell having a longitudinal cell axis;
   (b) a first cylindrical lens having a first central longitudinal axis oriented in a first common plane with the longitudinal cell axis and located on one side of said sample cell; and
   (c) a second cylindrical lens on another side of said sample cell, said second cylindrical lens having a second central longitudinal axis oriented transversely to the first common plane.

7. A sample cell assembly according to claim 6 including a plurality of second cylindrical lenses, each of said second cylindrical lenses having second central longitudinal axes each oriented transversely to the first common plane.

8. A sample cell assembly according to claim 7 wherein said second central longitudinal axes are oriented in a common plane that is perpendicular to the first common plane.

9. A sample cell assembly according to claim 8 including a plurality of light emitters, each light emitter operative to produce a beam of light along a respective optical axis that intersects said first longitudinal axis, said longitudinal cell axis and a respective second central longitudinal axis.

10. A sample cell assembly according to claim 9 wherein said light emitters are an array of fiber optic strands which receive light at first ends thereof from a light source and which have second end portions thereof facing said first cylindrical lens.

11. A sample cell assembly according to claim 10 wherein said fiber optic strands are bundles together at said first ends and receive light from a common light source.

12. A sample cell assembly according to claim 6 wherein said sample cell is a capillary tube.

13. A sample cell assembly adapted for use in spectroscopy of sample volumes in capillary chromatography, comprising:

(a) an elongated sample cell including a sidewall surrounding a longitudinally extending cavity that is operative to receive a flow of sample fluid therethrough, said sample cell having a longitudinal cell axis;

(b) a plurality of optic sets, each optic set including an emitter for generating a test beam of light, a photodetector operative in response to receipt of the test beam to generate a data signal corresponding thereto, a focusing lens operative to focus the test beam of light from the emitter onto the sample volume at a selected location along the longitudinal cell axis, and a collecting lens operative to receive the test beam after it has passed through the sample cell and to focus the test beam onto the respective photodetector, said optic sets being arranged such that the test beams of light pass through different sections of the cavity along said sample cell such that each optic set consecutively tests a selected sample volume of the fluid to produce a sample data corresponding to the selected volume; and (c) processing electronics operative to receive the sample data from each of the optic sets and to superimpose said sample data to produce an aggregate data for the selected sample volume.

14. A sample cell assembly according to claim 13 wherein said processing electronics includes an analog-to-digital converter associated with each said optic set and operative to receive data therefrom.

15. A sample cell assembly according to claim 13 wherein said focusing lens for each of said optic sets is defined by a common elongated lens.

16. A sample cell assembly according to claim 15 wherein said common elongated lens is a cylindrical lens having a central longitudinal axis oriented parallel to the longitudinal cell axis.

17. A sample cell assembly according to claim 16 wherein each said collecting lens is a second cylindrical lens, each said second cylindrical lens having a second longitudinal central axis oriented transversely to said longitudinal cell axis.

18. A sample cell assembly according to claim 17 wherein each said photodetector is elongated in a direction parallel to the second longitudinal central axes of said collecting lenses.

19. A method of measuring optical absorbance of light through a volume of sample material flowing in a flow direction through a sample cell, comprising the steps of:

(a) passing a plurality of test components of light through said sample cell each in a direction transversely to the flow direction and at different spaced locations therealong;

(b) providing a detector for each of said test components of light, each said detector operative to generate a detector output signal corresponding to intensity of a respective said test component; and (c) shifting phase of said detector output signals and thereby superimposing said detector output signals to create an augmented detector signal.

20. A method according to claim 19 wherein the step of shifting phase is accomplished by measuring velocity of said sample material through said sample cell in the flow direction and shifting each detector signal temporally an amount proportional to its spaced location and the velocity of said sample material.

21. A method according to claim 19 wherein the step of shifting phase is accomplished by identifying a target feature of each detector signal and shifting said detector signals to superimpose the target features with one another.

22. A method according to claim 19 wherein each of said detector signals is an analog signal and including the step of converting each detector signal to a digital signal prior to shifting the phase thereof.

23. A method according to claim 19 wherein the step of passing the plurality of test components of light through said sample cell includes the step of producing a beam of light and thereafter splitting said beam into said test components.

24. A method according to claim 19 wherein each of said test components is directed in a respective optical axis, said optical axes being parallel to one another.

* * * * *